United States Patent [19]
Beecher

[11] Patent Number: 4,784,654
[45] Date of Patent: Nov. 15, 1988

[54] URINARY COLLECTION SYSTEM AND IMPROVED FEMALE URINARY APPLIANCE

[75] Inventor: William H. Beecher, Elmhurst, Ill.

[73] Assignee: Illinois Tool Works, Inc., Chicago, Ill.

[21] Appl. No.: 442,207

[22] Filed: Nov. 16, 1982

[51] Int. Cl.⁴ .............................................. A61F 5/44
[52] U.S. Cl. .................................................... 604/329
[58] Field of Search ................................ 604/327–331, 604/349, 350, 351–354, 323, 335, 317–320, 327–331; 4/144.1–144.4; 128/343; 55/159

[56] References Cited

U.S. PATENT DOCUMENTS

| | | | |
|---|---|---|---|
| 3,194,238 | 7/1965 | Breece, Jr. | 604/329 |
| 3,335,714 | 8/1967 | Giesy | 604/329 |
| 3,529,599 | 9/1970 | Folkman | 604/323 |
| 4,160,383 | 7/1979 | Rauschenberger | 604/323 |
| 4,202,058 | 5/1980 | Anderson | 4/144.3 |
| 4,270,539 | 6/1981 | Frosch (Michard) | 4/144.3 |

OTHER PUBLICATIONS

Catalog at 'Gore-Tex Membrane Products', W. L. Gore & Assoc., Elkton, Md., 21921, 1980.

Primary Examiner—C. Fred Rosenbaum
Assistant Examiner—J. L. Kruter
Attorney, Agent, or Firm—Thomas W. Buckman; Neal C. Johnson

[57] ABSTRACT

An improved female urinary appliance is disclosed. The appliance includes a mouth surrounding a urine-receiving cavity, and a drainage channel. The mouth is adapted to be positioned within the labia folds of the user, in contact with the vestibular tissue around the meatus and held in place by gentle vacuum. A valve is preferably used in combination with the appliance, and includes an inlet and an outlet, for maintaining a preselected vacuum condition at the valve inlet and a predetermined pressure condition at the valve outlet is disclosed. In preferred use, the drainage channel is suitable connected in spaced relation to the valve inlet. The valve contains a flow control element adapted to control flow of urine from the cavity. While the mouth is held against the vestibular tissue by gentle vacuum, urine flowing through the appliance and valve entrains gas present in the cavity. In the cavity, a desired vacuum condition is maintained, over time, because the valve includes a semi-permeable membrane adapted to permit air and other gas to diffuse through a portion of the valve and thereby to counteract the effects of entrainment and relieve or maintain the vacuum condition at a predetermined level.

6 Claims, 3 Drawing Sheets

URINARY COLLECTION SYSTEM AND IMPROVED FEMALE URINARY APPLIANCE

REFERENCE TO RELATED APPLICATION

This application, assigned to Illinois Tool Works Inc. (ITW) of Chicago, Ill., is related to the application of Dr. Kenneth F. Hall and Mr. William Beecher (hereinafter referred to as the Hall Application) entitled "EXTERNAL FEMALE URINARY APPLIANCE", filed on the 16th day of November, 1982, having Ser. No. 442,068 U.S. Pat. No. 4,496,355, also partially assigned to ITW. This application hereby incorporates by reference the disclosures made in the Hall Application.

BACKGROUND OF THE INVENTION

This invention is directed to an improved urinary collection system and more particularly is directed to a novel arrangement of parts resulting in the creation of a partial vacuum between the collection device and the user.

This invention is also directed to an improved urinary collection appliance, and more particularly, the use of such appliance in the contemplated system.

Extensive research has been done in the medical area directed to the surface topology or geometry of certain areas of the female human form. It has, for example, been observed that a certain wall of muscle tissue (through which the clitoris, urethra and vagina project) is substantially identical in all adult human females. Accordingly, the Hall Application discloses an appliance (hereinafter referred to as the Hall Appliance), which when made of a suitable rubber-like material, and which is adapted to include a receptacle portion having an egaging surface substantially mated to the above mentioned wall of muscle tissue, is capable of sealingly engaging with such muscle tissue.

The Hall Application addresses various leakage problems associated with bodily engagement of urinary appliances with the female human form.

In addition to disclosing an appliance capable of providing such a sealing engagement with a female subject, the Hall Application relates to a female urinary appliance adapted to receive urinary discharge from the human subject and to convey such discharge into a urine bag, toilet or other receptacle. A mouth or opening on the Hall Appliance generally includes two sealing surfaces which are formed or shaped with peaks at opposite ends to engage the vestibular arch defined by Hall and two sealing surfaces which are formed or shaped so as to allow the appliance mouth to sealingly engage elliptical or ovoid surface portions of vestibular tissue. Such engagement is continuously made along such surface portions of vestibular tissue, first, near the clitoris, generally along the inner surfaces or undersides of the labia minora and proximate to but slightly below the orifice or meatus of the urethra. Such continuous engagement is secondly made also near the clitoris (the same region proximate the clitoris mentioned above), generally along the undersides of the labia minora (but disposed slightly outwardly in reference to the abovementioned labia minora surfaces) and below the orifice of the urethra (disposed slightly in the direction of the orifice of the vagina, in reference to the abovementioned engagement near the orifice of the urethra).

The sealing surfaces of the Hall Appliance are generally adjacent. The surface which is generally closer to the appliance mouth is disposed farther upwardly from the mouth than the surface which is disposed outwardly from the appliance mouth. The two surfaces unite and generally become one surface at one peak where the receptacle makes contact with the female form proximate to the clitoris, as described above. The generally adjacent surfaces co-operate to provide adequate sealing engagement of the Hall Appliance with the above described vestibular surface tissue.

The preferred embodiment of the Hall invention includes one means for preventing an appliance outlet (or an appliance drainage channel) from kinking which would adversely interfere with desired flow of urine through the drainage channel. This means is accomplished by providing a thin wall chamber having the thinnest wall section and the largest diameter; a transition zone of reduced diameter but slightly heavier wall thickness and finally a stem having the smallest diameter with the thickest wall portion.

In practicing the Hall invention, a problem has arisen and been identified. First of all, the Hall device is generally ovoid in plan view and has a pair of peaks located along the major axis which are interconnected by convex ridges disposed below said peaks. This device, much like a saddle, is adapted to be held against the vestibular tissue of the female, preferably, by the application of gentle pressure to the backside of the appliance. Such ridges and peaks are impressed or pushed into such vestibular tissue to ensure sealing engagement therewith, however, it has been found that certain females have found that the means for effecting such pressure application to be overly restrictive, or otherwise uncomfortable due to the deformation of the vestibular tissue. While the specific surface geometry of the Hall Appliance, is quite useful for providing sealing engagement with female vestibular tissue and for collecting urinary discharge from the female when gently held against the subject by pressure or force applied to the appliance backside, it does not lend itself to extended periods of usage due to its discomfort aspects.

Accordingly, an improved version of the Hall Appliance has been invented and is the subject matter of the instant application. Instead of an ovoid or egg-shaped external configuration the present invention relates to a pair of generally elliptical configured ridges having a gentler slope between opposite ends of the major axis of the device. This has been established through empirical application to a variety of female subjects to establish a semi-universal configuration for adult female human forms.

The improved appliance is also utilized as part of a system in which the appliance is initially applied by the application of gentle pressure to the backside of the appliance either manually or preferably by use of panties having an aperture centrally disposed in the crotch thereof. When using one preferred embodiment of the improved appliance it has been found desirable to interconnect, between the urine collector and the drainage channel of the improved appliance, anti-reflux valve means. As urine flows from the appliance through the connector tube and valve into the urine collector a vacuum is developed at the sealing surfaces of the appliance which is caused by the Venturi effect of urine flow. The vacuum level achieved is a function of the length of the connector tube, its diameter and the relative height of the appliance in relation to the urine collector and valve. The development of such a vacuum condition for the appliance at the bodily areas of engagement with the female enhance the seal with the vestibular tissues.

This vacuum effect can become cumulative during subsequent discharge of urine and may reach a level that can cause discomfort to the wearer. In solution of this problem the valve member can be provided with one or more vent ports utilizing hydrophobic filter means which provides a vent to permit ambient pressures to reach the inside of the system and to reduce the vacuum level experienced by the user.

In the urinary appliance art, means for causing an appliance to be secured (by suction) to bodily surfaces of a subject are known. U.S. Pat. No. 3,683,914 granted to Crowley, for example, teaches a valve which is adapted to create a vacuum condition at a valve inlet by maintaining realtively unvarying head or column of liquid in the valve. However, the valve of the U.S. Pat. No. 3,683,914 is not adapted to compensate for entrainment of air and other gas flowing downwardly through the valve of the '914 patent type. Although the valve of the '914 patent maintains a relatively unvarying column of liquid (in the valve), the above noted entrainment phenomenon results in a noticeable increase in the suction, over time, at bodily surfaces which are subject to the vacuum condition.

Conventional urine collectors take many forms and, as a rule, such urine collectors are generally sealed. A typical urine collector is usually a flattened and sealed container, or bag, initially containing very little, if any, air or other gas. Above-noted gas or vapor entrainment by the urine causes such collector to fill with air and other gas as it fills with urine and expands.

In practicing the invention of the improved appliance and its use in the system, a second problem has been identified in that eventually the quantity of air or other gas, which has been introduced via entrainment into such a sealed urine collector, interferes with the operation of a valve, of the U.S. Pat. No. 3,683,914 type. When an initially empty and sealed container is connected to the valve of the U.S. Pat. No. 3,683,914, no provision is made in the valve of the U.S. Pat. No. 3,683,914 to accommodate air or other gas being drawn by entrainment into the collector and which subsequently de-entrains from the urine and is eventually displaced from the urine collector and into the valve. Eventually, air or other gas accumulates within the valve and interferes with the anti-reflux operation of the valve of the U.S. Pat. No. 3,683,914.

OBJECTS AND SUMMARY OF THE INVENTION

Accordingly, one general object of this invention is to provide a system capable of managing incontinence in females without the use of indwelling catheters, diapers, etc. This is accomplished by providing an improved urinary appliance adapted to be sealingly engagable with the female human form, such engagement being enhanced by a vacuum or negative pressure condition.

A more specific object is that a gentle vacuum condition, for such an improved appliance, be somewhat constant and easily maintainable at the region where the appliance contacts and surrounds the vestibular tissue.

A more specific object is to provide a system including a discharge tube of predetermined height and a valve which is adapted to achieve a vacuum condition by maintaining a column of liquid having a preselected and relatively unvarying height.

A further object is to provide a valve which is generally unaffected, in operation, by air or other gas entering the valve via the valve outlet.

A related object is to provide such a valve having a valve body adapted to accept a hydrophobic filtered vent port which will permit air or other gas to diffuse therethrough.

Yet another general object of this invention is to provide an improved appliance, a valve and collection system which when used together co-operate to permit accomplishment of a particularly useful result.

Accordingly, a more specific object is, first, to provide an improved appliance which is sealingly engagable, such engagement being enhanced by predetermined vacuum conditions, with certain vestibular tissue of the female, and second, to provide a novel valve which provides the improved appliance with the predetermined vacuum condition desired.

While a multiplicity of known valve forms can be utilized the preferred illustrative embodiments are flapper type valves which require a predetermined head for operating the device and which are in a normally closed position. In one illustrative embodiment there are two filtered vent ports which include a hydrophobic filter that permits diffusion of gas therethrough but not liquids. In a preferred system that includes eight inches of vertical tubing between the appliance and the anti-reflux valve the following pressure/vacuum sequence occurs when the female appliance is in place. During the flow of urine a 5–10 cm water pressure (positive) is present in the portion of the system above the valve. When flow stops this pressure immediately drops to a negative value resulting in a vacuum level of 30–40 cm of water. The upstream hydrophobic filter vent in the valve then allows air to enter the system until equilibrium is reached. In the arrangement described this is approximately 8–10 cm of water vacuum. The system remains at this level, thereby ensuring no leakage between the appliance and the vestibular tissue, until the urine again flows freely through the appliance causing a rise of pressure in the system to a positive value of 5–10 cm of water and the cycle is repeated. The use of a second filter vent port on the downstream side of the valve permits diffusion of any gaseous pressure build up within the collection bag and thereby relieves any deleterious effect such pressures may have on the valve. An excessive pressure build up within the bag could cause the valve to remain in a closed position and thereby prevent introduction of additional fluid into the bag or alternatively, the development of a large head or column of liquid on the inlet side of the valve which might result in leakage around the appliance.

In summary, the improved appliance, according to the present invention, is a one piece external female urine collection device adapted to be positioned within the labial folds of the user, to be in contact with the vestibular tissue around the meatus and to be held gently and stabilized by mechanical means but enhanced by a gentle vacuum condition. The appliance comprises a generally elliptical and open cup-shaped member, and has a generally centrally disposed bore opening so that urine can flow freely through the member and the bore of the appliance. The upper surface of the appliance includes a generally elliptical and inwardly directed close-looped cuspated surface and a substantially continuous curved ridge extending upwardly therefrom. Portions of the appliance upper surface which are disposed away from the cuspated surface opposite the curved ridge and the curve ridge define dual upper portions of a cavity within the member. Such dual upper portions form an adjacent pair of sealing surfaces extending substantially continuously around the outer perimeter of the device. The inner surface is disposed farther upwardly, away from the cavity, relative to the outer surface. Depending from a backside of the member and integral therewith, and communicating with the bore opening and the cavity is a stem or cylindrical flange. The configuration of such stem is adapted to prevent interference of fluid flow through the bore opening by forming a thin walled chamber and a lower thick wall portion at the end of the chamber opposite the appliance and adapted to be connected to the tubing leading to the valve. Such heavier section and flexible thin walled chamber are adapted to avoid the kinking problem and prevent interference of fluid flow through the bore opening.

In addition to being generally elliptical in shape, the open cupshaped member has a gently sloping surface geometry which permits the appliance to be snugly secured to the above described vestibular tissue without excessive pressures and with such snug sealing application to be enhanced by a gentle vacuum condition imposed upon the appliance cavity.

BRIEF DESCRIPTION OF THE DRAWINGS

The foregoing, as well as other objects, features and advantages of the present invention will become more readily understood upon reading the following detailed description of the illustrated embodiments, together with reference to the drawings, wherein.

DETAILED DESCRIPTION OF THE INVENTION

Referring to the drawings, and initially to FIGS. 1-5, an illustrative embodiment of the improved appliance will now be discussed.

Figure 1:
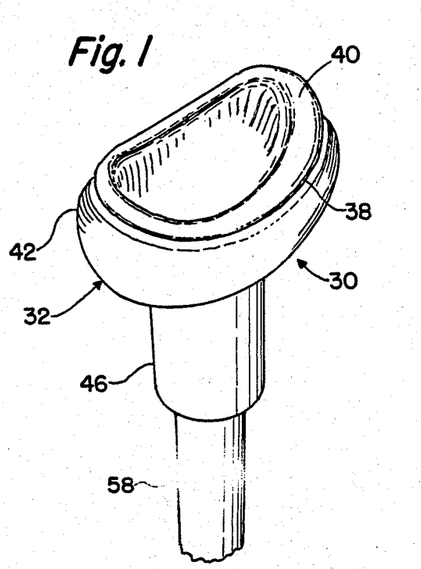
FIG. 1 is a perspective view of a preferred embodiment of the improved female urinary appliance, in accordance with the present invention.

The appliance 30 is a one-piece external female urine collection device adapted to be positioned within the labial folds of the user (generally along the inner surfaces or undersides thereof) and adapted to be in contact with the vestibular tissue around the meatus defining the urethral opening. The appliance 30 includes a generally elliptical and open cup-shaped member 32 with a tapered upper chamber 34 terminating at its narrow end in a generally centrally disposed bore opening 36 so that urine can flow through the member 32 and the appliance 30. The upper surface geometry of the appliance 32 includes a generally elliptical and inwardly-directed close-looped cuspated surface 38 and a substantially continuously curved ridge 40 extending upwardly therefrom. Portions of the appliance 30 upper surface which are disposed away from the cuspated surface 38 opposite the curved ridge 40 are designated as surface 42, define and form an adjacent pair of sealing surfaces 40, 42. The inner surface 40 is disposed farther upwardly, away from the cavity 34, relative to the outer surface 42.

Depending substantially perpendicular from a backside (referred to generally by the reference numeral 44; see FIGS. 2 and 4) of the member 32 and integral therewith is a relatively thin-walled cylindrical flange or tubular member 46 which communicates with the bore opening 36 and provides the cavity 34 with a drainage channel. The flange 46 is oriented about the axis 48 (see FIG. 4). Further details on the cylindrical flange or tube 46 will be set forth hereinafter.

Figure 2:
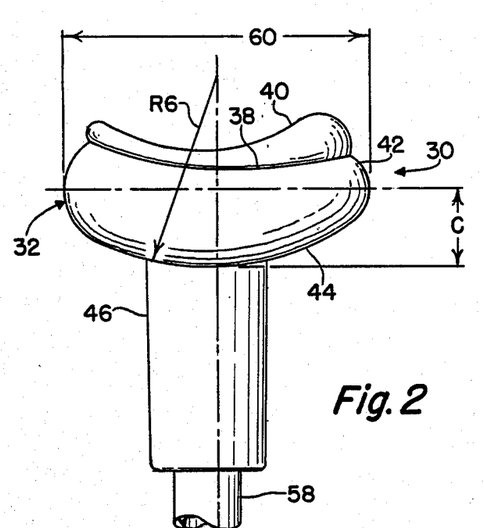
FIG. 2 presents a side view of the appliance shown in FIG. 1.
Figures 3, 4, 5:
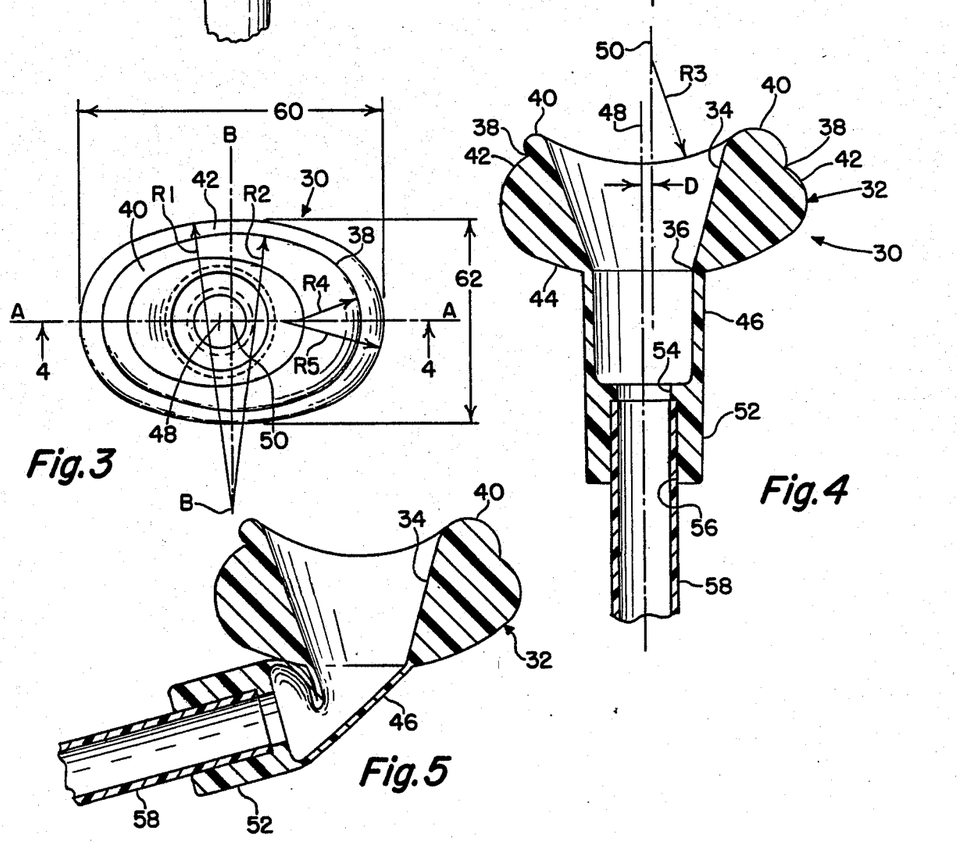
FIG. 3 is a top view of the appliance shown in FIG. 1.
FIG. 4 is a side elevational view in section taken along the line 4—4 in FIGS. 3 and showing one means for attaching the collection tubing to the female appliance.
FIG. 5 is a side elevational view in section of the device shown in FIG. 4 and illustrates the anti-kinking feature of the present invention.

The sealing surfaces 40, 42 and member 32 are oriented about an axis 50 which is substantially parallel to the axis 48 and which is displaced therefrom by the distance D (FIG. 4). As viewed from above the appliance 30 (FIG. 3), the projections of the sealing surfaces 40, 42 are generally elliptical. The appliance 30 is seen to have a major axis "A", which passes through axes 48 and 50 and a minor axis "B" which is oriented laterally in relation to the axis 48 but perpendicular in relation to the major axis "A" (FIG. 3). Both of these axes "A", "B" form a plane which is substantially perpendicular to the axis 48. Moreover, referring to FIG. 2, it will be seen that the lateral projection of the appliance 30 is also generally elliptical along a second plane which either contains or is substantially parallel to the axis 48 with a semiminor axis "C" oriented vertically, as is the axis 48.

Generally in the plane formed by the axes "A", "B" (FIG. 3), or in a plane (not shown) generally parallel thereto which is perpendicularly disposed in relation to the axis 50, is an origin (arbitrarily presented in FIG. 3) for a first radius of curvature R1, which generally describes the elliptical external edge boundary of the appliance 30. A second radius of curvature R2, having a second origin, located in position generally as described above for the first origin, generally describes the location of the cuspated surface 38 separating the adjacent sealing surfaces 40, 42. Within the plane formed by the axes "A", "C" (FIG. 2) and from a point of origin, located on the axis 50, exterior to the appliance 30 (FIG. 4) a third radius of curvature R3 describes the gently sloping surface geometry (of the appliance 30) at the entrance to the cavity 34 where the appliance 30 generally makes engagement with the vestibule and labial folds of the female. As best seen in FIG. 3, the end surfaces of the appliance 30 are defined by points of origin falling on the axis "A" wherein the radius R5 defines the end external geometry of the appliance 30 while the radius R4 defines the cuspated surface 38.

Vacuum sealing of the improved appliance 30 with the female is generally achievable when the following values are maintained. Referring now to FIGS. 2 and 3, the length 60 along axis "A" ranges from about 1.5 inches to about 1.88 inches (about 4.01 to about 4.78 cm). Length 60 is preferably about 1.73 inches (about 4.39 cm). The width 62 taken along axis "B" ranges from about 1.03 inches to about 1.23 inches (about 2.62 to about 3.12 cm). The width 62 is preferably about 1.13 inches (about 2.87 cm). The nominal projection height "C" ranges from about 0.37 inches to about 0.47 inches (about 0.94 to about 1.19 cm). "C" is preferably about 0.42 inches (about 1.07 cm). The offset relationship defined by the distance "D" ranges from about 0.070 inches to about 0.086 inches (about 0.178 to about 0.218 cm). "D" is preferably about 0.078 inches (about 0.198 cm). R1 ranges from about 1.50 inches to about 1.80 inches (about 3.81 or about 4.57 cm). R1 is preferably about 1.65 inches (about 4.19 cm). R2 ranges from about 0.975 inches to about 1.175 inches (about 2.48 to about 2.98 cm). R2 is preferably about 1.075 inches (about 2.73 cm). R3 ranges from about 0.915 inches to about 1.115 inches (about 2.32 to about 2.83 cm). R3 is preferably about 1.015 inches (about 2.58 cm). R4 ranges from about 0.393 to about 0.48 inches (about 1.00 to 1.22 cm). R4 is preferably about 0.4375 inches (about 1.11 cm). R5 ranges from about 0.450 inches to about 0.550 inches (about 1.143 to about 1.397 cm). R5 is preferably about 0.500 inches (about 1.27 cm). R6 ranges from about 1.485 inches to about 1.815 inches (about 3.77 to about 4.61 cm). R6 is preferably 1.650 inches (about 4.191 cm).

The adjacent sealing surfaces 40, 42 which are continuous and provide dual adjacent sealing surfaces around the entire periphery of the appliance 30, permit the appliance 30 to sealingly and continuously make contact with the female by engaging with the inner portions of the labial folds and the remainder of the abovementioned vestibular tissue.

Referring now more particularly to the cylindrical tube-like flange 46, as best seen in FIGS. 4 and 5, the flange 46 is a thin walled member having a wall thickness in the range of about 0.025 to about 0.035 inches and preferably about 0.031 inches with the length of the thin walled portion, as measured from the backside 44 of the member 32, being only slightly greater than the inner diameter of the flange 46. A thick wall extension 52 includes a central aperture 54 and a counterbore lower bore 56 capable of accepting a length of tubing 58 having an internal bore substantially equal to the bore of the opening 54 whereby free unrestricted flow into the tubing is permitted. The tubing 58 is fixed within the counterbore 56 by suitable means known in the art such as adhesive or heat sealing. As can be best seen in FIG. 5 deflection of the flange 46 results in a slight closure to the internal diameter thereof by a flexing of one side and stretching of the other side without a closing off of the bore and thereby permitting a free passage unimpeded of the urine through the inside of the flange 46, the thickened portion 52 and the tubing 58 to a suitable collector. This anti-kink feature can be readily accomodated and integrally fabricated within a female urine collection device of the type disclosed hereinabove.

Figure 6:
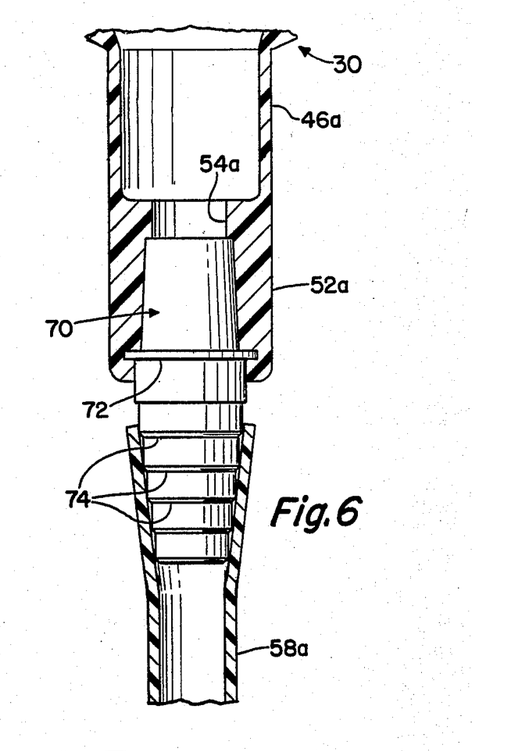
FIG. 6 is a modification to the present invention showing the use of an insert molded connector usable for attaching discharge tubing to the female appliance.
Figure 7:
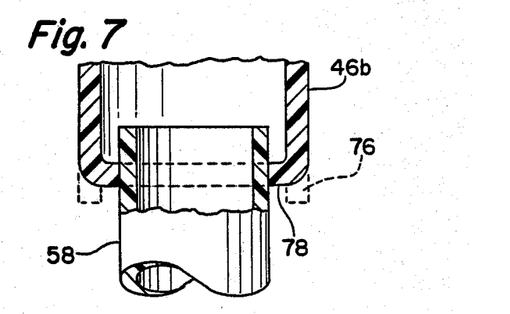
FIG. 7 is a further embodiment of the means for connecting discharge tubing to the female appliance.
Figure 8:
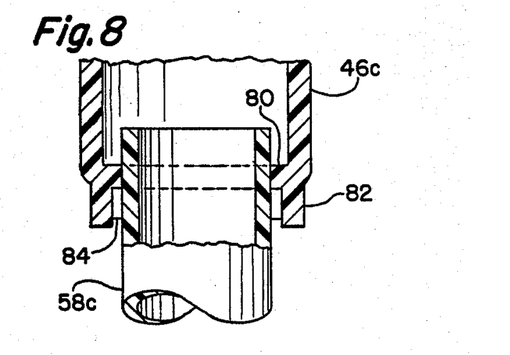
FIG. 8 is still another embodiment of further means for connecting the discharge tubing to the female element.

Referring now to FIGS. 6–8 additional embodiments of the connecting means are shown and wherein similar parts are designated by similar numerals with the additions of the suffixes a, b and c. In FIG. 6 the flexible flange 46a includes a thickened portion 52a having a centrally disposed bore 54a and a tubing connector 70 with an enlarged flange 72 insert molded within the thickened portion 52a. The tubing connector 70 includes at its free exposed end a plurality of stepped shoulders 74, of the type well known in the art, for expanding and providing a sealed acceptance and passage to the interior of tubing 58a which has been expanded thereover. The connector 70 has a central bore, not shown, substantially equal to the diameter of the bore 54a to provide unimpeded through flow of urine from the female appliance, not shown.

A second embodiment of connecting means discloses the thin wall flange 46b, in fragmentary section, and in which the terminal ends 76, initially coaxial therewith, are bent inwardly to form an inwardly directed flange 78 secured to the tubing 58b by adhesive or heat sealing means.

FIG. 8 is still another embodiment in which the thin wall flange 46c, shown in fragmentary section, is provided with an inwardly directed flange 80 and a downwardly directed cylindrical flange 82. The inwardly directed flange 80 has a central bore adapted to accept tubing 58c while the downwardly directed flange 82 forms a chamber or pocket between itself and the tubing 58c to accept a sealing ring 84 of either adhesive or other known O-ring types of sealing and retaining mechanisms.

The anti-kink feature in each of the last three embodiments shown in FIGS. 6, 7 and 8 all function in the same fashion as that shown in FIG. 5, namely, a thin wall flange terminated by a thick wall rigid portion which will orient the bending and stretching in the thin wall portion 46a, b and c without kinking or total shut off of the urine flow therethrough.

Figure 9:
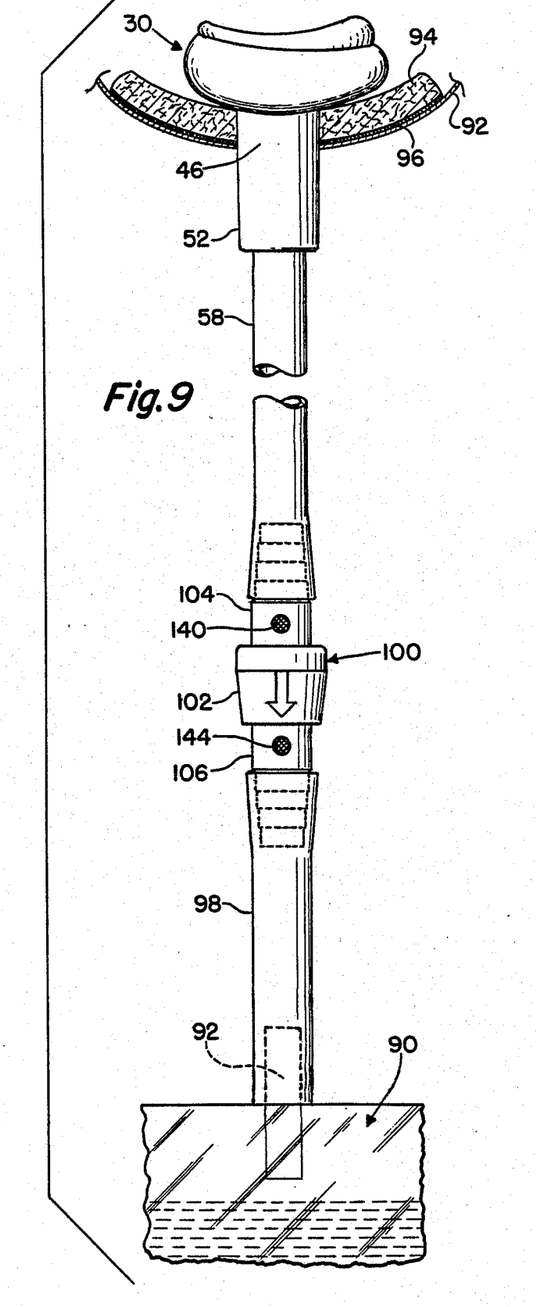
FIG. 9 is a side elevational view in partial section of the system utilizing the female collection appliance of the present invention.
Figures 10, 11, 12, 13, 14:
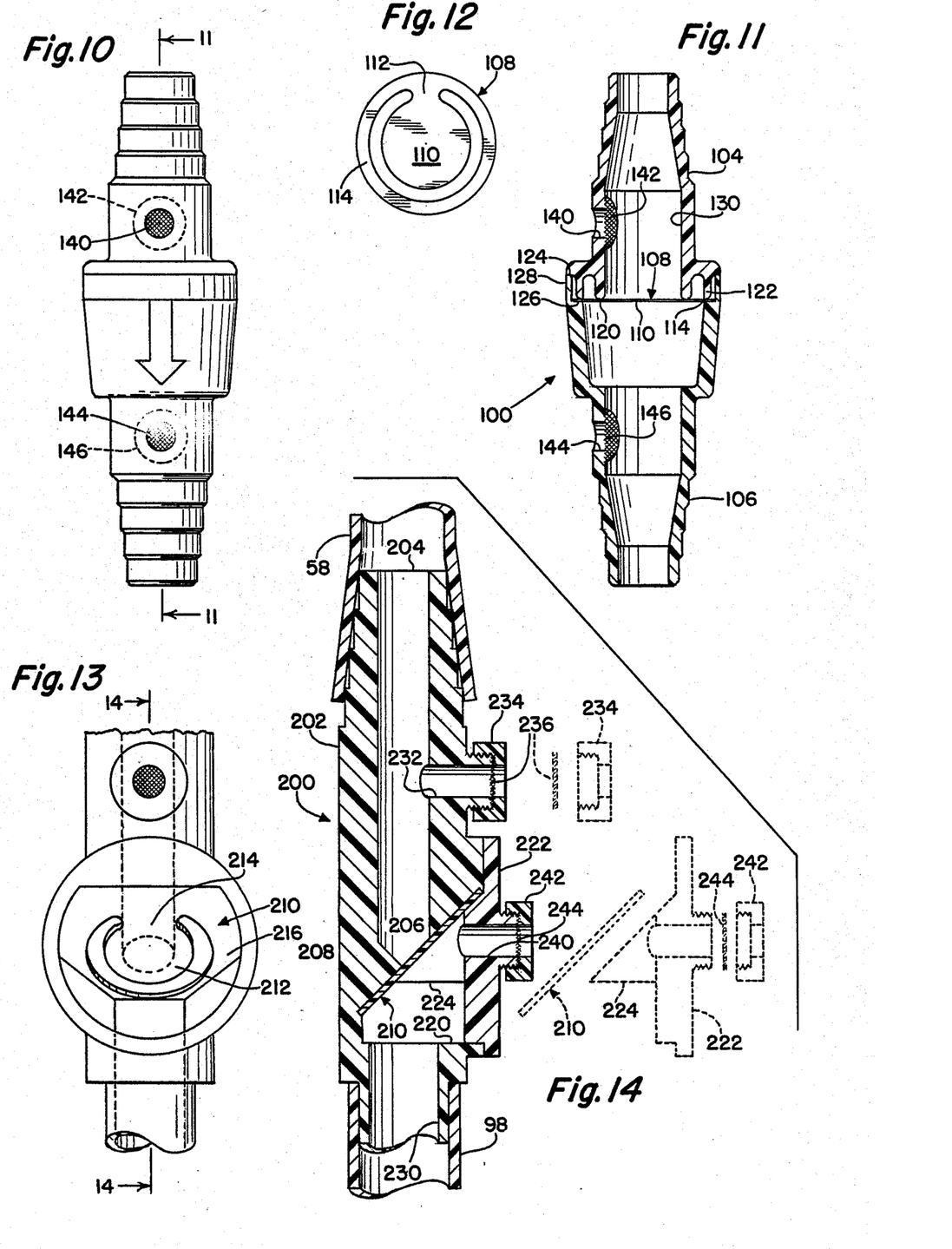
FIG. 10 is a side elevational view of a valve and filter mechanism used in the system shown in FIG. 9.
FIG. 11 is an elevational view in section, taken along line 11—11 of FIG. 10.
FIG. 12 is a plan view of the flapper valve used in the filtered valve shown in FIG. 11.
FIG. 13 is an elevational view of a second form of valve, in partial section, of the type usable in the system shown in FIG. 9.
FIG. 14 is an exploded side sectional view taken along line 14—14 of the valve shown in FIG. 13.

Referring now to FIGS. 9–14 and particularly FIG. 9 wherein the system of the present invention is generally disclosed. The appliance 30 is preferably connected to a urine collection vessel or urine collector bag 90 (FIG. 9). The urine collector 90 is usually a sealed and initially flat plastic sack or bag of the type well known in the art. The appliance 30 can be initially secured to desired vestibular tissue of the female, as set forth hereinabove, by imposing a gentle securing and compression means such as a pair of panties 92 (only the crotch being shown in section) which have a centrally disposed aperture to accept the downwardly extending portions 46 and 52. Preferably a mini-pad 94 having an adhesive layer 96 for securement to the panties 92 serves to stabilize the collector 30 and to maintain it in the predetermined desired location. This is supplemented by imposing a gentle vacuum condition upon the cavity 34 of the appliance 30. One known method of imposing such a vacuum condition upon the cavity 34 is by maintaining a preselected head of liquid (such as urine) beneath the appliance 30. To accomplish this the anti-reflux valve of the present invention is preferably interconnected between the appliance 30 and the collector 90 to control the head of urine and vacuum. The novel valve 100 includes a valve structure 102 which defines a valve inlet 104 and a valve outlet 106 and encloses a flapper-type valve 108. One preferred form of flapper valve 108 includes a flap 110 which is integral through a neck 112 with a circumferential circular collar 114, see FIGS. 11 and 12. As best seen in FIG. 11, the valve inlet 104 includes an annular axially extending rounded edge flange 120 serving as a seat against which the flap 110 can position itself in a normally closed relation while outboard thereof there is a second flange 122 axially directed and terminating in the same plane as flange 120 and diametrially outwardly thereof a shoulder 124. Valve outlet 106 includes a counterbore forming shoulder 126 and an axially extending flange 128. The valve inlet 104 and valve outlet 106 with their co-axial arrangement cause the flange 122 and shoulder 126 to grip the collar 114 in a tight sealed realtionship. Such sealing can be accomplished by either bonding with a commerically available adhesive or alternatively by heat sealing the two plastic portions together. By maintaining the axial extent of flanges 122 and 128, to accomodate the thickness of the flapper valve 108 a normally closed positive seating occurs between the flap 110 and the axially directed flange 120 serving as the seat for flap 110. As urine flows downwardly a predetermined head of urine is established within the tube 58 and acts against the flap 110 and causes it, upon establishment of such head, to bias to an open position in a known manner.

The flap 110 engages, substantially covers, and seals against the seat formed by flange 120 and thereby maintains an initial head or column of urine (or other liquid) in the tubular portion 130 of valve inlet 104 (liquid not shown). The flapper type valve 108 is made of a commercially available suitably resilient substance which permits the initial head or column of liquid to assume a predetermined value. The preferred flapper-type valve is made of an approximately 0.005 inch (approximately 0.13 m) thick polyester film. The neck 112 and collar 114 cooperate to bias the flap 110 against the seat 120 against the weight of the column of liquid in the tubular portion 130 thereby preventing such liquid from flowing out of the tube 130 via the valve outlet 106.

As the column of liquid increases in height, the weight of liquid in the tube 130 eventually increases to the point where the flap 110 is urged away from the seat 120. Whereupon the height of the column of liquid quickly decreases in the tube 130 and tube 58 as the liquid flows past the flap 110. Most of this liquid usually immediately flows out the valve outlet 106, preferably filling the collector 90 connected thereto. The height of liquid in the tube 130 is quickly reduced to a point where the flap 110 can again support the weight in the tube 130. Whereupon, the flap 110 again moves upwardly against the seat 120, through the biasing action of neck 112, and seals against the seat 120.

It has been noted however, that the passage of urine through the appliance 30 and the tube 58 and valve 100 develops through a Venturi-like action an initial vacuum condition which is imposed by the appliance 30 to the body of the female, and as the female discharges additional urine into the cavity 34 of the improved appliance 30, a marked feeling of increasing discomfort is felt (over time) at the vestibular tissue to which the improved appliance 30 has been applied. It has been observed, indirectly, that as urine is discharged into the cavity 34 of the improved appliance 30, such urine entrains some of the air and certain other gases initially present in the cavity 34. Such entrainment depletes the cavity 34 of an initial amount of quantity of air or other gas and serves to increase, over a period of time, the vacuum sensation.

Between the flap 110 and the improved appliance 30, the inlet portion 104 of the valve structure 100 includes a first vent 140 through which air and certain other gas is permitted to pass so that an initial vacuum condition, imposed upon the cavity 34 of the improved appliance 30, can be maintained.

Such a vent includes a hydrophobic filter or membrane 142 covering the vent 140 and permitting the ingress or egress of gases but, because of its hydrophobic nature, prevents the passage of liquids such as urine. Within the tubular portion 130 the height of liquid is generally well above the vent 140 and it is the hydrophobic filter 142 which prevents liquid from leaking out of the tubular portion 130. The filter membrane 142 has a pore size such that most gas is permitted to diffuse therethrough, but such that urine or other liquids are not permitted to noticably or appreciably diffuse therethrough. When the pore size ranges from about 3 microns to about 15 microns (a preferred pore size range), no diffusion of urine has been noted.

The illustrated embodiment of the system including the improved appliance 30 with its outlet flange 46, 52 is connected to a piece of hollow and flexible plastic tubing 58, of suitable length, is usually used to connect the appliance 30 to the valve 100 in accordance with the present invention. In most applications a length of about 8 inches for the tubing 58 is preferred. During the flow of urine a 5–10 cm of water pressure (positive) is present in the portion of the system above the valve. When the discharge of urine flow stops, this pressure immediately drops to a negative value resulting in a vacuum level of 30–40 cm of water. The upstream hydrophobic filter vent 140 in the valve 100 then allows air to enter the system until a semi-equilibrium condition is reached. In the arrangement described this is approximately 8–10 cm of water vacuum. The system remains at this level, insuring tight engagement of the appliance 30 with the vestibular tissue, until urine again flows causing a rise of pressure in the system to a positive value of 5–10 cm of water and the cycle is repeated. The equilibrium vacuum level is determined in part by the length of tube and vertical distance the appliance is located above the valve. The top connector in the valve (above the upstream vent) generally has an inside diameter of from about b 0.175 inches to about 0.280 inches with a preferred optimum inside diameter of approximately 0.200 inches to achieve the pressure/vacuum sequence described above.

It should be noted, that as the female discharges urine into the cavity 34 of the improved appliance 30 and as urine flows down the tube 58 and through the valve 100, it has been observed that minute bubbles can be seen in the column of urine. Such bubbles first appear at the liquid side of the semi-permeable membrane 142 have been seen to pass through the vent opening 140 and inwardly in the urine in the tubular portion 130 of the valve 100. Without the vent opening 140 being present on the tubular portion 130 no such bubbles were observed.

Furthermore, it has been observed that the height of the column of liquid in the valve 100 and the tubing 58, in addition to being caused by the biasing action of the neck 112 of the flapper-type valve 108, is a surface tension phenomenon of the particular liquid. For example, when the tubing 54 used is specifically a commercially available extruded latex having a nominal internal diameter (I.D.) of 5/16 inches (nominally about 0.313 inches or about 0.794 cm), the height of female human urine in the valve 100 and the tubing 58 was observed to extend generally about 3 to about 4 inches above the vent inlet 140. Such a particular type of commercially available tubing is held to an I.D. tolerance of 1/64 inches (about 0.016 inches or about 0.40 cm). Yet for a nominal tubing I.D. of ⅜ inches (nominally about 0.375 inches or about 0.953 cm), it was observed that within such tubing 58 and in the tubular portion 130 of the valve 100 above the vent inlet 140 no such height or column of urine could be maintained. The column of urine in the tubing 58 extended upwardly from the flapper-type valve 108 only generally up to the vent opening 140. Furthermore, for a nominal tubing I.D. of ¼ inches (nominally about 0.250 inches or about 0.635 cm), it was noted that the bubbles (observed in the urine) could not move upwardly in the tubular portion 130 of the valve 100. The nominal 5/16 tubing I.D. experiment was repeated and a substantial amount of a commercially available soap solution was added to the column of urine; and the height of urine in the tube 130 and tubing 58 was observed to be markedly less than above noted. For the tubing 58, the preferred nominal I.D. is 5/16 inches. The preferred I.D. at the inlet end portion 104 of the valve 100 is about 0.200 inches (about 0.508 cm).

The tubing 58 is preferrably substantially translucent while the valve 100 is preferrably made of a suitable and clear plastic, and is preferrably transparent.

A second suitable length of flexible plastic tubing 98, connects the outlet end portion 106 of the valve 100 to a suitable inlet connection 92 on the urine collector 90. As urine flows downwardly through the outlet valve portion 106 of the valve 100 and fills the collector 90, entrained air and other gas eventually de-entrains, begins to accumulate in the collector 90 and eventually is displaced out of the collector 90 and up the outlet tube 98 where it can interfere with the operation of the flapper-type valve 108.

Accordingly, the outlet portion 106 of the valve 100 preferrably includes a second vent opening 144 to permit gas in the outlet tube 98 to pass through the wall of the valve structure 100. This valve vent opening 144 also includes and is covered by a hydrophobic filter membrane 146 which forms a liquid seal thereat. The second membrane 144 is preferrably of the same substance and has the same pore dimension as the first membrane 142. It should be noted that both of these membranes can be either insert molded during the fabrication of the inlet portion 104 and the outlet portion 106 of valve 100 or alternatively can be formed as part of a closure cap (not shown) which would be inserted into the valve ports 140 and 144. It will be appreciated that the downstream hydrophobic filter vent 144 allows air to escape from the collector/leg bag 90 thus permitting a higher fluid level before a back pressure is developed that will impair the proper operation of the system, i.e. entrained air serving to act against the flap 110 to cause it to remain in a closed position resulting in an undesirable head of liquid within the tubing 58 and possible leakage of liquid from the collector unit 30.

While not shown, it has been found that a valve having a single downstream vented port, i.e. vent port 144 with a hydrophobic filter membrane 146, will work adequately to de-entrain air and other gases from the bag and because of the impositive nature of flapper valve 108 will permit sufficient ambient air to enter the system to partially relieve the vacuum condition where the appliance 30 engages the vestibular and labial tissue.

Such an embodiment would be identical to that previously disclosed with valve 100 but with the elimination of the upper vent port 140 and its associated hydrophobic filter 142.

The first embodiment of valve and filter (shown in FIGS. 10–12) described hereinabove is but one example of an in line valve and filter which can be used. A second embodiment of such a filtered valve can be seen in FIGS. 13 and 14. Where the first valve member, namely inlet portion 104 and outlet portion 106 can be molded in a simple bank mold with minimal side action for ports 140 and 144, the second embodiment of FIGS. 13 and 14 requires slightly greater tooling expense due to the multiplicity of parts involved. This embodiment of the valve 200 includes a main body 202 having an inlet end 204 suitable shaped to engage the interior of the tubing 58 and an exit opening 206 entering into a biased or canted seat 208. A flapper valve 210 of a design substantially identical to the prior described valve 108 includes a flap 212 engaging the seat 208 and covering the opening 206, a hinge 214 and an encircling body 216. A side opening 220 forming a chamber in the body 202 which includes the seat 208 is closed by a cover member 222 having flange means 224 for engaging the peripheral body portion 216 of the valve 210 to maintain it in tight engagement with the seat 208 but allowing freedom of movement of the flap 212 to open and provide venting through the opening 206. The main body includes an outlet opening 230 adapted to be engagable with the discharge tube 98 that connects with the collector 90.

In this embodiment there is a vent port 232 upstream of the valve 210 and includes an apertured cap 234 capable of accepting a hydrophobic filter 236 which serves the same function as the filters in the previous embodiment. Similarly a downstream vented port 240 is covered by a ported cap 242 which carries a similar hydrophobic filter membrane 244. The function operation of this valve is substantially equivalent to the first embodiment when used in the system shown in FIG. 9.

It can be appreciated that the flapper-type valves 100 and 200 are but two embodiments of valves adapted to permit liquid to flow in only one direction as required by the present invention. Variations in modifications of flapper valves of this type are generally well known in the art, however, the use of such a valve having a vented port with a hydrophobic filter therein in the environment shown herein is not known to exist in the prior art. A system of the type disclosed provides a gentle mechanical means for initially engaging the vestibular mucosa of the female anatomy and after first discharge of urine ensures continued seal with such vestibular and labial tissues by the maintenance of the vacuum condition. The deleterious effects of the vacuum are generally overcome by the hydrophobic filtered vent ports which reduce the discomfort to the patient but insure an adequate vacuum condition for sealing purposes. The system is economical to fabricate and is reusable through the observance of general cleanliness and known techinques. The female collection device can be injection molded of Kraton ® material manufactured by Shell Oil Company; polyethylene; as well as other injection moldable soft rubber-like materials which are comfortable to the female form. The valve elements can be injection molded of suitable plastic materials of a wide variety known to the marketplace and inert to urine.

While specific sizes have been set forth for a collection device that is usable with the "normal adult human female" it should be recognized that narrower units can be used with petite females and that devices which bear the same general proportions but which have a smaller length and width than the sizes set forth are being developed for use with immature females, i.e. teenagers who suffer incontinence.

What has been illustrated and described herein is a novel system and an improved female urinary appliance. While the valve and the appliance of the present invention have been illustrated and described with reference to several preferred embodiments, the present invention is not committed thereto. On the contrary, alternatives, changes or modifications may become apparent to those skilled in the art upon reading the foregoing descriptions. Accordingly, such alternatives, changes and modifications are to be considered as forming a part of the present invention insofar as they fall within the spirit and scope of the appended claims.

I claim:

1. An external urine collection system comprising soft and pliable upper member having means to sealingly engage surface tissue of an incontinent patient, a lower vessel for receiving and storing urine, a generally tubular urine flow passageway connecting said upper member with said lower vessel, valve means in said passageway for restricting flow of fluids towards said upper member, and hydrophobic venting means downstream of the valve means for allowing dissipations of excessive pressure downstream of the valve in said passageway while preventing egress of liquid from said system, said urine flow passageway having a vertical head above said valve of approximately eight inches to maintain a vacuum seal between said upper member and body, a column of urine is maintained above said valve providing said head.

2. A urine collection system of claim 1 wherein said valve means is a flapper-type valve element and said valve is located at a distance from said upper member of about eight inches.

3. A urine collection system of claim 1 wherein said vent venting means has a pore dimension of about 3 to 15 microns.

4. An external urine collection system comprising soft and pliable upper member having means to sealingly engage surface tissue of an incontinent patient, a lower vessel for receiving and storing urine, a tubular urine flow passageway connecting said upper member with said lower vessel, valve means in said passageway for restricting flow of fluids towards said upper member, and hydrophobic venting means upstream of the valve means for allowing dissipations of excessive pressure in said passageway above said valve means while preventing egress of liquid from said system, said urine flow passageway having a vertical head above said valve of approximately eight inches to maintain a vacuum seal between said upper member and body, a column of urine is maintained above said valve providing said head.

5. An external urine collection system comprising an upper member having means to sealingly engage surface tissue of an incontinent patient, a lower vessel for receiving and storing urine, a tubular urine flow passageway connecting said upper member with said lower vessel, valve means in said passageway for restricting flow of fluids towards said upper member, and two hydrophobic vents, one vent downstream of the valve means for allowing dissipation of excessive positive pressure in said vessel, and another vent upstream of said valve means for allowing dissipation of excessive negative pressure in said passageway while preventing egress of liquid from said system, said urine flow passageway having a vertical head above said valve of approximately eight inches to maintain a vacuum seal between said upper member and body, a column of urine is maintained above said valve providing said head.

6. An external urine collection system comprising a soft pliable cup shaped upper member having a sealing surface to engage surface tissue of an incontinent female patient, a lower flexible vessel for receiving and storing urine, a generally tubular urine flow passageway connecting said upper member with said lower vessel, a check valve in said passageway for preventing urine from flowing toward said upper member, at least one vent in said passageway, said vent for allowing dissipation of excessive pressure from and for preventing egress of liquid from said system, said urine flow passageway having a vertical head above said valve of approximately eight inches to maintain a vacuum seal between said upper member and body, a column of urine is maintained above said valve providing said head.

* * * * *